United States Patent [19]

Bonn

[11] Patent Number: 5,382,230
[45] Date of Patent: Jan. 17, 1995

[54] VASCULAR ACCESS SHEATH FOR INTERVENTIONAL DEVICES

[75] Inventor: Joseph Bonn, Strafford, Pa.

[73] Assignee: Thomas Jefferson University, Philadelphia, Pa.

[21] Appl. No.: 808,003

[22] Filed: Dec. 16, 1991

[51] Int. Cl.$^6$ .............................................. A61M 1/00
[52] U.S. Cl. .................................... 604/32; 604/248; 137/613; 251/212; 251/340
[58] Field of Search ............... 604/51, 52, 250, 255, 604/246, 248, 264, 280, 30-34; 251/212, 88, 339, 340; 137/613

[56] References Cited

U.S. PATENT DOCUMENTS

| | | | |
|---|---|---|---|
| 2,171,576 | 9/1939 | Larry et al. | 137/613 |
| 2,321,336 | 6/1943 | Tondreau | 251/212 |
| 3,496,878 | 2/1970 | Hargest et al. | 604/31 |
| 3,513,846 | 5/1970 | Gallo | 604/31 |
| 3,527,226 | 9/1970 | Hakim | 604/280 |
| 4,267,835 | 5/1981 | Barger et al. | 604/250 |
| 4,493,709 | 1/1985 | Smith | 604/250 |
| 4,540,411 | 9/1985 | Bodicky | 604/169 |
| 4,580,573 | 4/1986 | Quinn | 128/657 |
| 4,769,018 | 9/1988 | Wilson | 604/248 |
| 4,771,772 | 9/1888 | DeWitt | 604/266 |
| 4,779,625 | 10/1988 | Cole | 128/673 |
| 4,781,698 | 11/1988 | Parren | 604/246 |
| 4,820,280 | 4/1989 | Berch et al. | 604/248 |
| 4,820,288 | 4/1989 | Isono | 604/280 |
| 5,009,391 | 4/1991 | Steigerwald | 251/149.1 |
| 5,078,688 | 1/1992 | Lobodzinski et al. | 604/248 |
| 5,084,031 | 1/1992 | Todd et al. | 604/248 |
| 5,106,363 | 4/1992 | Nobuyoshi | 604/280 |
| 5,125,893 | 6/1992 | Dryden | 604/171 |
| 5,158,553 | 10/1992 | Berry et al. | 604/246 |
| 5,190,534 | 3/1993 | Kendell | 604/30 |

Primary Examiner—Randy C. Shay
Attorney, Agent, or Firm—Woodcock Washburn Kurtz Mackiewicz & Norris

[57] ABSTRACT

A vascular access sheath is provided for introducing catheters, stents, and other interventional devices into blood vessels. The invention comprises a stiff tubular catheter segment, which is designed to remain outside the body, having two hemostatic valves, most preferably of an iris valve design disposed at each end. A flexible sheath extends from one of the valves for insertion into the blood vessel. In operation, the valves are opened and closed one at a time, to allow relatively large devices to be introduced into the blood vessel without the valve pressing against the devices and with minimal loss of blood.

11 Claims, 1 Drawing Sheet

VASCULAR ACCESS SHEATH FOR INTERVENTIONAL DEVICES The present invention relates to apparatus for use with interventional devices such as catheters to aid in their insertion into blood vessels.

BACKGROUND OF THE INVENTION

Currently existing vascular sheaths were initially designed to safely and easily introduce angiographic catheters of relatively small diameters, e.g., 4–7 French (1.3–2.3 mm) percutaneously into arteries and veins. The advent of angioplasty balloon catheters led to the development of sheaths having inner diameters as large as 8–9 French (2.6–3.0 mm) to accommodate the early large balloon catheters. The basic design of the hemostatic valve typically provided at the proximal end of the sheath has changed only minimally during this time, the modifications being in materials and minor changes to improve hemostasis.

As familiar to those of skill in the art, the introduction of vascular stents (Palmaz, Wallstent, Strecker, Gianturco), percutaneously inserted vena cava filters (Titanium Greenfield, Bird's Nest, Simon Nitinol LGM Venatech), and atherectomy catheters (Simpson, T. E. C.) stimulated the development of vascular sheaths ranging in inner diameter from 10 to 14 French (3.3 to 4.6 mm). These larger sheaths have been designed either with the same hemostatic valves as the original smaller sheaths, or without a valve at all in the case of certain filter sheaths, since these latter sheaths are placed in the lower pressure venous system.

It has become apparent that passing stents and atherectomy catheters through the original-design hemostatic valve into the arterial system requires a stiff cylindrical sleeve to open the valve and prevent damage to the stent or atherectomy catheter as it passes through the valve. This is both cumbersome and results in a momentary massive blood leak under arterial pressure, as hemostasis is lost because the valve is opened by the sleeve.

U.S. Pat. No. 4,580,573 to Quinn and U.S. Pat. No. 4,540,411 to Bodicky both disclose catheter introducers having a single elastic valve. Such valves are designed to press tightly against a catheter as it is inserted and thereby attempt to prevent blood loss. Such valves have been found, however, to be inadequate for introducing stents and filters, which would be damaged by such pressure. On the other hand, if such valves are left open as devices are passed through them, a significant loss of blood would occur. U.S. Pat. No. 5,0009,391 to Steigerwald discloses a valve assembly for introducing catheters having two elastic disc valves. The discs are normally closed, but permit a catheter to pass through them while pressing tightly against the catheter. However, as was the case with other elastic valves described above, these designs are inadequate for introducing stents and filters since these devices would be damaged by such pressure.

A need therefore remains for a vascular sheath for introducing interventional devices into the vascular system, without pressing tightly against the interventional device as it is inserted while preventing a significant loss of blood.

SUMMARY OF THE INVENTION

The present invention provides a vascular sheath, comprised of a plastic tube with a hemostatic valve at one end, designed to be placed percutaneously into an artery or vein to gain access for the purpose of introducing other catheters or therapeutic interventional devices to treat various occlusive vascular abnormalities. The vascular sheath of the present invention is designed to protect the vessel entry site as well as the interventional device during the placement, manipulation and removal of the device while maintaining hemostasis. In particular, the disclosed vascular sheath is designed so that it is preferably used in conjunction with relatively larger interventional devices such as vascular stents and atherectomy catheters, and is specially configured to provide hemostasis through a "chamber lock" design rather than the single hemostatic valve as found in the vascular sheaths of the prior art.

The present invention therefore represents a major modification to existing vascular sheaths in that two hemostatic devices, most preferably of an iris valve design, are disposed at either end of a stiff tubular catheter structure, which is designed to remain outside the body. In a preferred embodiment, the stiff tubular structure has a tubular side arm joined to it to allow the lumen to be evacuated of air, fluid or blood, or to allow injection of fluids or, for example, radiographic contrast agents into the sheath. This segment is bonded end-to-end to a suitable flexible tubular sheath material which is placed through the arteriotomy or venotomy to reside in the patient's vessel.

The stiff tubular structure of the vascular sheath disclosed acts as an air lock functions in a spacecraft by providing an intermediate chamber that can be selectively closed between two areas of different pressure. After the flexible portion of the sheath is inserted in the usual fashion over a guidewire, a first iris valve closest to the patient's skin is closed to prevent blood from backing up into the sheath. This allows opening a second iris valve at the end of the sheath furthest away from the patient's skin without blood loss since the first valve is closed. The stent, atherectomy catheter, vena cava filter or other interventional device is then inserted through the second iris valve into the chamber, and the second iris valve is closed to provide sufficient friction for the catheter to be hemostatic. With the interventional device now in the chamber and the second iris valve, the first iris valve is opened to permit blood flow to fill the chamber. A tubular side arm allows aspiration of the chamber to evacuate any air and to insure that it is completely filled with blood. At this point, the interventional device is advanced out of the chamber and through the intravascular sheath into the blood vessel.

As noted above, the chamber provided within the vascular sheath of the present invention is stiff enough to resist kinking which might damage the stent, atherectomy catheter or filter while it resides within the chamber. The chamber is also preferably sufficiently radiolucent to allow fluoroscopy to penetrate and permit inspection of the condition or position of the device while it is still in the chamber. The chamber is also long enough between the first and second iris valves to fully accommodate the longest interventional device that will be inserted. The iris valves are most preferably of an internal diameter that, when open, is equal to the internal diameter of the chamber and of the intravascular sheath so as not to restrict the size of the device which could be introduced. In a preferred embodiment, a ring or handles allow the valves to be opened much like the f-stop ring on a camera lens controls the iris diameter.

Accordingly, it is an object of the present invention to provide a novel vascular access sheath for introducing devices into blood vessels with minimal loss of blood and without the sheath exerting significant pressure on the interventional device as it is inserted.

This and other objects of the present invention will become apparent from the following, more detailed description of the present invention.

DESCRIPTION OF THE PREFERRED EMBODIMENTS

Figure 1:
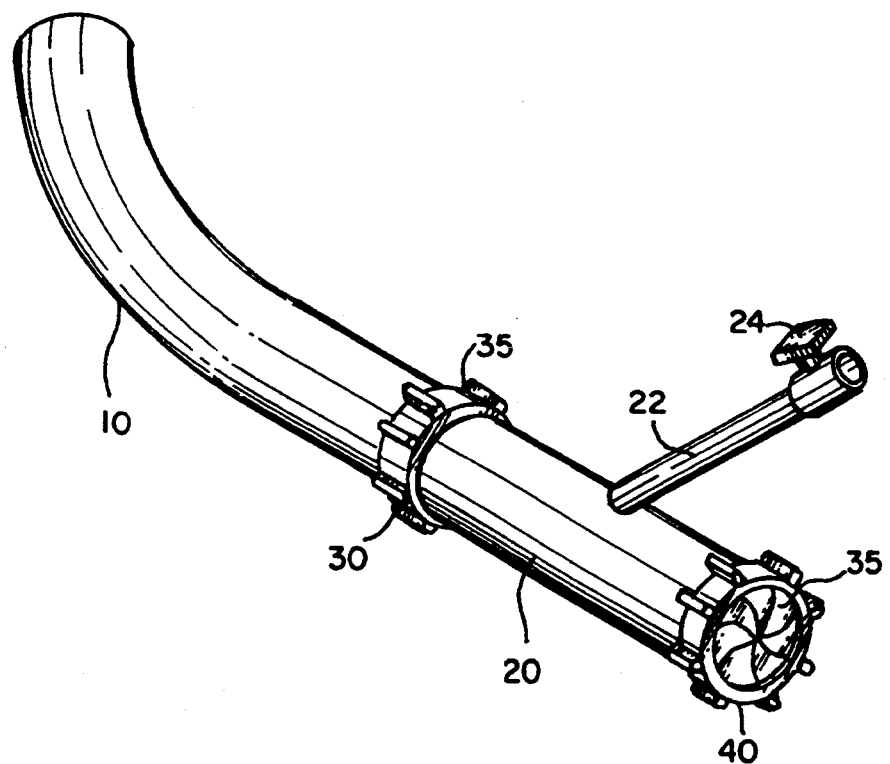
FIG. 1 is a perspective view illustrating a vascular access sheath made in accordance with the present invention.

The present invention provides a vascular sheath for introducing devices into blood vessels without a significant loss of blood. Thus, referring now to FIG. 1, there is shown a preferred embodiment of a sheath made in accordance with the present invention comprising a rigid hollow tube 20 having a first iris valve 40 bonded to the rigid hollow tube 20 at its proximal end. A second iris valve 30 is bonded to the rigid hollow tube 20 at its distal end. A flexible hollow tube 10 for insertion into the patient is bonded to the second iris valve 30 at its proximal end. The distal end of the flexible tube 10 is inserted into the patient, preferably using a guidewire in the manner known to those of ordinary skill. The first and second iris valves 30,40 are normally in a closed position as seen in FIG. 1. Each of the iris valves 30,40, has an external control means 35 which enables the user to place each iris valve 30,40 in an open position, such that interventional devices can pass through the iris valves 30,40, without their exerting pressure on the interventional device. An iris valve manufactured by Applied Urology (Laguna Hills, Calif.) is an example of a valve suitable for use in the present invention.

In certain preferred embodiments, a hollow tubular side arm 22 extends from the side of the rigid tube 20 to allow air to be evacuated from the rigid tube 20 and fluid to be injected into the rigid tube 20 if desired. A stopcock 24 is attached to the end of the side arm 22 to selectively provide a seal.

The length of the rigid tube 20 is preferably longer than longest device to be inserted. In a preferred embodiment, this length is about 3.0 inches (70–80 mm). The inner diameter of the rigid tube 20, and the inner diameter of both of the iris valves in their open positions, is most preferably greater than the outer diameter of the largest interventional device to be inserted, so that the device can be inserted without the rigid tube 20 or iris valves 30,40 exerting pressure against the device. In a preferred embodiment, this inner diameter ranges between approximately 7–12 French (2.3–4.0 mm).

The present invention also provides methods of inserting an interventional device into a patient, Thus, in use, the sheath of the present invention is inserted in the usual fashion over a guidewire such that the flexible tube 10 enters a blood vessel. The distal second iris valve 30 is closed to prevent blood from backing up into the sheath. The proximal first iris valve 40 is then opened and a stent, atherectomy catheter, vena cava filter, or other interventional device can then be inserted through the first iris valve 40 into the rigid tube 20. The first iris valve 40 is closed against the interventional device with enough friction to be hemostatic. The distal iris valve 30 is then opened to blood flow, which would fill the chamber. In certain embodiments, a stopcock 24 may be opened on a side arm 22 to allow aspiration of the rigid tube 20 to evacuate any air and to insure that it was filled with blood. At this point, the interventional device may be advanced out of the rigid tube 20 and through the flexible sheath 10 into a blood vessel of the patient. The interventional device may later be removed using the sheath of the present invention in the reverse manner.

While specific forms of the present invention have been selected for the purposes of illustration, one of ordinary skill in the art will recognize that various departures may be made to the examples set forth herein without departing from the scope of the present invention, which is defined more particularly in the appended claims.

What is claimed:

1. A sheath for introducing an interventional device into a vessel of a patient comprising:
    a rigid tubular structure, having a proximal end, a distal end, and a passage therethrough;
    a first valve having a proximal end, a distal end and a passage therethrough, the passage having a diameter continuously variable by operation of a means for controllably opening and closing said passage to selectively permit fluid flow in an open position or preclude fluid flow in a fully closed position, wherein said distal end of said first valve is connected to said proximal end of said rigid tubular structure and said proximal end of said first valve is a sealable port for inserting an interventional device into and through the rigid tubular structure;
    a second valve having a proximal end, a distal end and a passage therethrough, the passage having a diameter continuously variable by operation of a means for controllably opening and closing said passage to selectively permit fluid flow in an open position or preclude fluid flow in a fully closed position, wherein said proximal end of said second valve is connected to said distal end of said rigid tubular structure and said distal end of said second valve is a sealable port for inserting an interventional device into the patient; and
    a flexible tubular structure, having a proximal end, a distal end, and a passage therethrough, wherein said distal end of said second valve is connected to said proximal end of said flexible tubular structure,
    whereby said first and second valves may be selectively opened to create an opening having a diameter to admit the interventional device through at least one of the valves while maintaining hemostasis by a sliding seal.

2. The sheath of claim 1 wherein said rigid tubular structure is comprised of a radiolucent material.

3. The sheath of claim 1 wherein said sheath further comprises a side arm port having first and second ends, wherein said rigid tubular structure further comprises an opening, and one end of said side arm port is connected to said rigid tubular structure at said opening to permit flow of fluid through said side arm port.

4. The sheath of claim 3 wherein said first end of said side arm port further comprises a stopcock for controlling the flow of fluid through said tubular port.

5. The sheath of claim 1 wherein said rigid and flexible tubular structures have inner diameters ranging from about 7 to 12 French (2.3–4.0 mm).

6. The sheath of claim 1 wherein said first and second valves are comprised of iris valves.

7. The sheath of claim 6, wherein said iris valves comprise an external control means for controllably opening and closing said passage through said rigid tubular structure.

8. Apparatus for inserting an interventional device into a patient comprising:
   a rigid tube having a proximal and a distal end;
   a first valve having an orifice and being connected to the proximal end of the tube, the first valve comprising means for adjusting a diameter of the orifice thereby creating a sealable port for inserting the interventional device;
   a second valve having an orifice and being connected to the distal end of the tube, the second valve comprising means for adjusting a diameter of the orifice thereby creating a sealable port for inserting the interventional device; and
   a flexible tube having a proximal end connected to the second valve,
   whereby the first and second valves are operated to selectively isolate the rigid tube from fluid flow in a closed position, and to open the orifice of the second valve to permit fluid flow, and to selectively open the orifice of the first valve a diameter sufficient to receive the interventional device while maintaining hemostasis by a sliding seal.

9. The apparatus of claim 8, further comprising a side arm tube connected to the rigid tube for selectively permitting a fluid flow comprising aspirated gas and fluid from the rigid tube and also for introducing fluids into the rigid tube.

10. The apparatus of claim 9, wherein the side arm tube comprises a stopcock.

11. A sheath for introducing an interventional device into a vessel of a patient comprising:
   a rigid tubular structure having a first and second end;
   a first valve connected to the first end of the rigid tubular structure and a second valve connected to the second end of the rigid tubular structure for controlling flow therethrough by adjusting a continuously variable orifice of at least the first valve, the orifice defining a sealable port capable of receiving the interventional device so that the interventional device can be inserted into and through the rigid tubular structure; and
   a flexible tube connected to the second valve
   wherein the orifice of the first and second valves is selectively moveable between an open position to permit flow and a closed position to preclude flow,
   the first and second valves being capable of receiving the interventional device so that the interventional device can be inserted into the rigid tubular structure through the orifice of the first valve when the second valve is closed such that the sealable port maintains hemostasis when the second valve is opened to permit the interventional device to be inserted through the rigid tubular structure into the flexible tube.

* * * * *